United States Patent

LeBoeuf et al.

[11] Patent Number: 6,015,842

[45] Date of Patent: *Jan. 18, 2000

[54] METHOD OF PREPARING FOLDABLE HYDROPHILIC OPHTHALMIC DEVICE MATERIALS

[75] Inventors: Albert R. LeBoeuf; Mutlu Karakelle, both of Fort Worth, Tex.

[73] Assignee: Alcon Laboratories, Inc., Fort Worth, Tex.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/910,966

[22] Filed: Aug. 7, 1997

[51] Int. Cl.[7] ............... C08F 2/50; C08F 20/18; C08F 26/10; C08F 20/10
[52] U.S. Cl. .................. 522/64; 522/75; 522/79; 522/167; 522/182; 523/106; 523/108
[58] Field of Search .................. 522/64, 84, 182, 522/28, 75, 18; 523/106, 108

[56] References Cited

U.S. PATENT DOCUMENTS

| | | | |
|---|---|---|---|
| 4,324,744 | 4/1982 | Lechtken et al. | 522/64 |
| 4,390,676 | 6/1983 | Loshaek | 526/313 |
| 4,447,520 | 5/1984 | Henne et al. | 522/64 |
| 4,528,311 | 7/1985 | Beard et al. | 524/91 |
| 4,795,461 | 1/1989 | Lindqvist et al. | 523/106 |
| 5,145,884 | 9/1992 | Yamamoto et al. | 522/14 |
| 5,353,628 | 10/1994 | Chirila et al. | 523/106 |
| 5,433,746 | 7/1995 | Namdaran et al. | 623/6 |
| 5,470,932 | 11/1995 | Jinkerson | 526/312 |
| 5,610,204 | 3/1997 | Lai | 522/44 |
| 5,741,831 | 4/1998 | Keita et al. | 523/106 |
| 5,891,931 | 4/1999 | Leboeuf et al. | 522/64 |

*Primary Examiner*—Susan W. Berman
*Attorney, Agent, or Firm*—Patrick M. Ryan

[57] ABSTRACT

Foldable, hydrophilic, ophthalmic device materials are cured by exposure to blue light using a benzoylphosphine oxide photoinitiator.

15 Claims, 2 Drawing Sheets

METHOD OF PREPARING FOLDABLE HYDROPHILIC OPHTHALMIC DEVICE MATERIALS

FIELD OF THE INVENTION

This invention relates to photopolymerizable acrylic ophthalmic device materials. In particular, this invention relates to the use of benzoylphosphine oxide initiators in blue-light curing of foldable hydrophilic ophthalmic device materials.

BACKGROUND OF THE INVENTION

The two most common types of polymerization initiators for ophthalmic device materials are thermal initiators and photoinitiators. Typical thermal initiators, including free radical initiators such as peroxides, initiate polymerization as temperature is increased. In some cases, two or three temperature tiers are involved such that curing involves a schedule of temperature/time combinations. Thermal initiation generally requires holding the monomer composition at elevated temperatures for lengthy periods of time. Total cure times of twenty-four hours are not unusual. See, for example, U.S. Pat. No. 5,290,892.

Photoinitiators generally offer the advantage of relatively short cure times and, unlike thermal initiators, can be used at ambient conditions, eliminating the need for high-temperature equipment or special ovens. Photoinitiators are activated by light of one or more specified wavelengths, rather than heat. Photoinitiation of ophthalmic lens materials is known. See, for example, U.S. Pat. No. 5,290,892.

The most common types of photoinitiators known or used for curing ophthalmic lens polymers are probably ultraviolet UV-sensitive photoinitiators. UV-sensitive photoinitiators are, however, generally not suitable for use with lens materials that contain a UV-absorbing chromophore. UV-absorbing chromophores present in an ophthalmic lens composition can interfere with the ability of UV-sensitive photoinitiators to efficiently cure the composition. Today, UV-absorbing chromophores are frequently incorporated in ophthalmic lens materials in order to reduce or block UV light from reaching the retina. Although methods are known for temporarily "blocking" UV absorbing chromophores during processing, thereby preventing interference with a UV-initiator, these methods require that the UV-absorber be "un-blocked" after the composition is cured. The UV chromophore can be "un-blocked" by either chemical or thermal means. "Un-blocking" is generally complicated and can add 4–6 hours to processing times, offsetting some or all of the time advantages offered by photoinitiators.

In addition to UV-sensitive photoinitiators, visible-light initiators are also known. For example, U.S. Pat. No. 5,224,957 discloses photopolymerizable compositions useful in forming an intraocular lens in situ. The compositions are delivered into the natural lens capsule or a thin plastic shell substitute and then polymerized. The reference compositions contain 90–99.99% by weight of at least one polyfunctional acrylic and/or methacrylic acid ester. Suitable acid esters include bisphenol A or bishydroxypolyalkoxy bisphenol A derivatives lengthened with ethylene oxide or propylene oxide.

The compositions of the '957 patent are cured using photoinitiators which absorb light in the range 400–500 nm. Suitable initiators include alpha-diketones, in particular camphorquinone, benzil and phenanthrene quinone, and mono and bisacylphosphine oxides. According to the '957 patent, particularly preferred initiators are "for example 2,4,6-trimethylbenzoyldiphenylophosphine oxide and bis-(2,6-dichlorobenzoyl)-4-n-propylphenylphosphine oxide or bis-(2,6-dichlorobenzoyl)-4-n-butylphenylphosphine oxide" (see Col. 3, lines 12–16).

International Patent Application Publication No. WO 96/28762 also discloses photocurable compositions comprising acrylic components. The compositions contain specified amounts of di(meth)acrylates, poly(meth)acrylates, urethane(meth)acrylates, and oligomeric di(meth)acrylates based on bisphenol A or bisphenol F. The photoinitiator may be "any photoinitiator which forms free radicals when irradiated suitably." Suitable classes include benzoin ethers; acetophenones; benzil; anthraquinones; benzoylphosphine oxides (e.g., 2,4,6-trimethylbenzoyldiphenylphosphine oxide); benzophenones. Photoinitiators particularly suitable for use with argon ion lasers include 2,4,6-trimethylbenzoyldiphenylphosphine oxide.

SUMMARY OF THE INVENTION

The present invention relates to methods for preparing foldable hydrophilic ophthalmic device materials that contain a benzoylphosphine oxide photoinitiator and a hydrophilic device-forming materials selected from the group consisting of 2-hydroxyethylmethacrylate; 2-hydroxyethylacrylate; N-vinylpyrrolidone; glyceryl methacrylate; glyceryl acrylate; polyethylene oxide mono- and dimethacrylates; and polyethylene oxide mono- and diacrylates. The methods comprise activating the benzoylphosphine oxide photoinitiator with a blue-light source.

Among other factors, the present invention is based on the finding that such ophthalmic device materials are effectively cured using a blue light source and the benzoylphosphine oxide initiator, 2,4,6-trimethylbenzoyldiphenylophosphine oxide. In contrast, when camphorquinone, which has a greater absorbency in the blue-light region than 2,4,6-trimethylbenzoyldiphenylophosphine oxide, is used in place of the benzoylphosphine oxide initiator, the same ophthalmic device materials are not efficiently cured.

DETAILED DESCRIPTION OF THE INVENTION AND PREFERRED EMBODIMENTS

Figure 1:
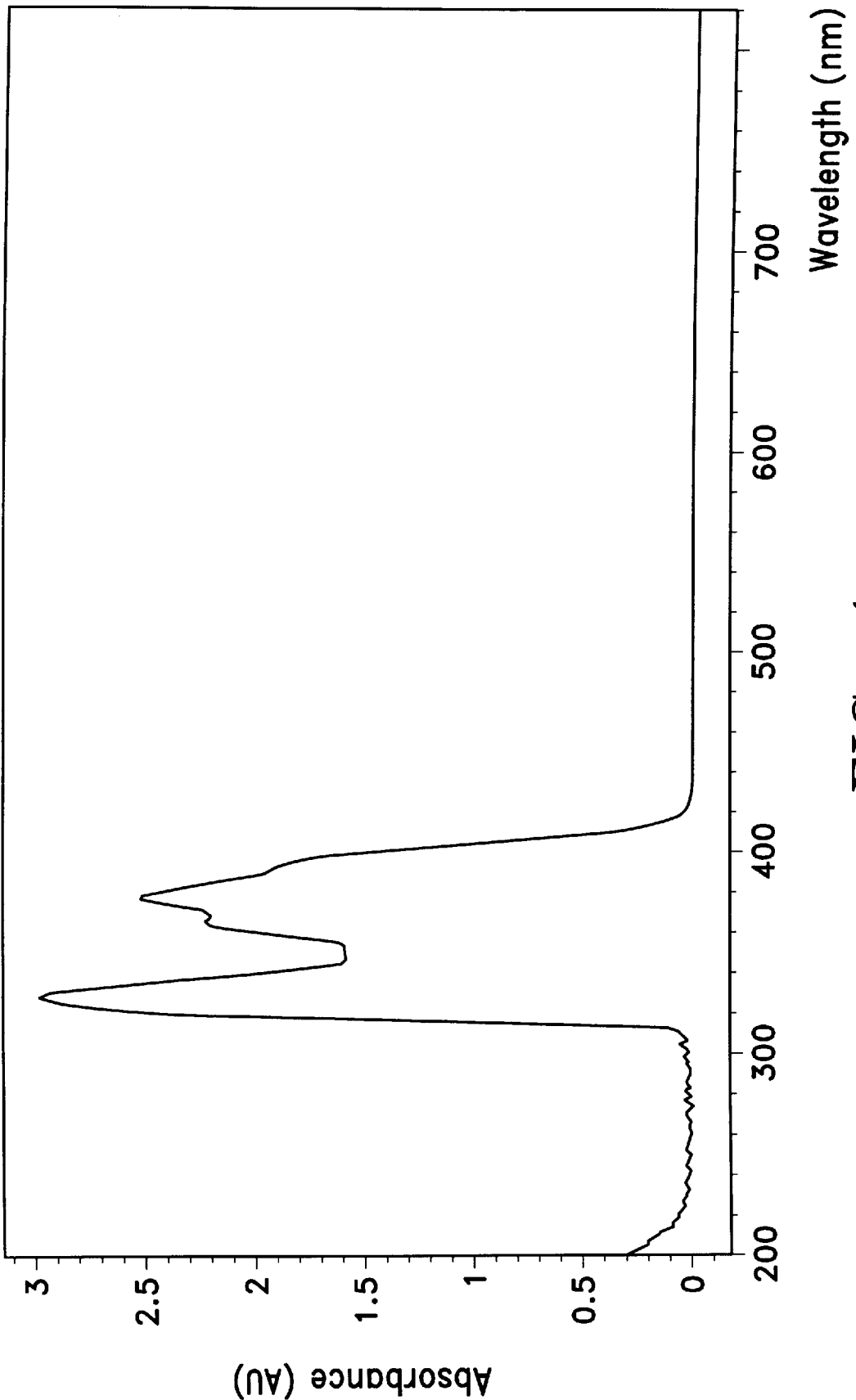
FIG. 1 shows a sample UV-visible spectrum of the benzoylphosphine oxide initiator 2-4-6-trimethylbenzoyldiphenylophosphine oxide in a 2-phenylethyl acrylate solvent.

According to the present invention, foldable, hydrophilic ophthalmic device materials comprising one or more hydrophilic monomers selected from the group consisting of 2-hydroxyethylmethacrylate; 2-hydroxyethylacrylate; N-vinylpyrrolidone; glyceryl methacrylate; glyceryl acrylate; polyethylene oxide mono- and dimethacrylates; and polyethylene oxide mono- and diacrylates; are prepared using a blue-light source and a benzoyl-phosphine oxide initiator. First, an ophthalmic device material mixture comprising one or more of the hydrophilic a monomers listed above and a benzoylphosphine oxide initiator is prepared. After the mixture is prepared, it is exposed to a blue-light source for a time sufficient to cure the device material.

The hydrophilic monomers specified above are known and are commercially available or can be synthesized using known procedures. Preferred hydrophilic monomers are 2-hydroxyethylmethacrylate and N-vinylpyrrolidone.

The exact amount of hydrophilic monomer present in the foldable ophthalmic device materials of the present invention will vary depending upon the identity of the hydrophilic monomer(s), the identity of any other device-forming monomer(s) present in the materials, and the desired mechanical properties. For example, foldable intraocular lenses are preferably made from polymers having a glass transition temperature no greater than normal room temperature, e.g., about 20–25° C., in order that the lenses can be rolled or folded conveniently at room temperature. Glass transition temperature is determined at room temperature using a differential scanning calarimeter at a heating rate of 10° C./min. Additionally, materials exhibiting an elongation of at least 150% when measured at room temperature using an Instron tensile tester at a cross-head speed of 50 cm/min) are preferred for use in foldable intraocular lenses because such lenses must exhibit sufficient strength to allow them to be folded without fracturing. For foldable intraocular lens applications, polymers having an elongation of at least 200% are more preferred.

In general, the foldable ophthalmic device materials of the present invention will contain a total of at least 50% (wtw) of one or more of the specified hydrophilic monomers. Preferably, the device materials will contain one or more hydrophilic monomers in an amount totaling 70% (w/w) or more, and most preferably, 80% (w/w) or more.

Device-forming monomers other than the specified hydrophilic monomers optionally may be included in the compositions of the present invention. Many such ophthalmic device-forming monomers are known. Any known device-forming monomer may be used if it is compatible with the chosen hydrophilic monomer(s) and does not interfere with the ability of the benzoylphosphine oxide photoinitiator to cure the composition when exposed to blue light. Suitable device-forming monomers other than the hydrophilic monomers specified above include, but are not limited to: acrylic acid, $C_1$–$C_8$ arylalkylacrylates, $C_1$–$C_8$ alkylacrylates, $C_1$–$C_8$ cycloalkylacrylates, N-alkylacrylamides (where alkyl=$C_1$–$C_4$), phenoxyalkylacrylates (where alkyl=$C_1$–$C_8$), and their corresponding methacrylates.

As in the case of the hydrophilic monomer(s), the amount of any other device-forming monomers present in the ophthalmic device materials of the invention will vary depending upon the identity of the chosen hydrophilic monomer(s), the identity of the chosen optional device-forming monomer(s), and the mechanical properties desired for the polymerized ophthalmic material. In general, for foldable intraocular lens applications, the ophthalmic device materials of the present invention may contain about 45% (w/w) or less, and preferably about 30% (w/w) or less, of device-forming monomers other than the specified hydrophilic monomers.

In addition to the device-forming monomer(s), the device materials of the present invention contain a benzoylphosphine oxide as a photoinitiator. Benzoylphosphine oxide initiators are known and are commercially available. Examples of benzoylphosphine initiators include 2,4,6-trimethylbenzoyldiphenylophosphine oxide; bis-(2,6-dichlorobenzoyl)-4-N-propylphenyl-phosphine oxide; and bis-(2,6-dichlorobenzoyl)-4-N-butylphenylphosphine oxide. Most preferred is 2,4,6-trimethyl-benzoyldiphenylophosphine oxide, commercially available as Lucirin® TPO from BASF Corporation (Charlotte, N.C.).

The amount of benzoylphosphine oxide initiator in the device materials of the present invention will depend upon the identity of the other ingredients in the materials, the light flux, and other processing conditions such as the desired curing time and the presence of inhibitors such as oxygen. In general, however, the amount of benzoylphosphine oxide initiator will be about 3% or less, preferably about 2% or less, and most preferably about 1%.

If desired, ultraviolet absorbing chromophores may be included in the ophthalmic device materials of the present invention. Such chromophores prevent or inhibit UV light from damaging the eye. In the case of intraocular lenses, UV absorbers allow the light absorbance of an intraocular lens to approximate that of the eye's natural lens. The ultraviolet absorbing chromophore in the device material of the present invention can be any compound which absorbs light having a wavelength shorter than about 400 nm, but does not absorb any substantial amount of visible light, and which is compatible with the device-forming monomer(s) present in the material. The ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl)-benzotriazoles. It is preferred to use an ultraviolet absorbing compound that is copolymerizable with the device-forming monomers described above so that it will be covalently bound to the polymer matrix. In this way, possible leaching of the ultraviolet absorbing compound out of the device and into the interior of the eye is minimized. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'-methyl phenyl) benzotriazole.

Although not essential, the ophthalmic device materials of the present invention may optionally contain one or more copolymerizable cross-linking monomers. The use of cross-linking monomers is preferred. If desired, suitable cross-linking monomers include almost any terminally ethylenically unsaturated compound having more than one unsaturated group. Suitable cross-linking agents include, for example: ethyleneglycol dimethacrylate; diethylene glycol dimethacrylate; ethyleneglycol diacrylate; allyl methacrylates; allyl acrylates; 1,3-propanediol dimethacrylate; 1,6-hexanediol dimethacrylate; 1,4-butanediol dimethacrylate; polyethyleneoxide mono- and diacrylates; and polyethyleneoxide mono- and dimethacrylates, and the like. In some cases where a polyethyleneoxide diacrylate or dimethacrylate is chosen as a hydrophilic device-forming monomer, sufficient cross-linking may be achieved without the need for any supplemental cross-linking agent. A preferred cross-linking agent is 1,4-butanediol diacrylate (BDDA). The amount of cross-linking agent generally will be less than about 10% (w/w) or less, preferably about 5% (w/w) or less.

Blue-light absorbing compounds are also optionally included in the device materials of the present invention. The blue-light absorbing compound, e.g. yellow dyes, should only be used in an amount at which they do not substantially interfere with the blue light source's ability to activate the benzoylphosphine oxide initiator. The presence of a blue-light absorber may necessitate an increased amount of benzoylphosphine oxide initiator. Preferably, blue-light absorbers are copolymerizable with the device-forming monomers. Suitable polymerizable blue-light blocking chromophores include those disclosed in U.S. Pat. No. 5,470,932.

The device materials of this invention are prepared by forming a mixture of the device-forming monomer(s) (the hydophilic monomer(s) and any optional device-forming monomer(s)), the UV-absorbing (if desired) chromophore, and the benzoylphosphine oxide initiator, along with any other suitable ingredients, in the desired proportions. The mixture can then be introduced into a mold of suitable shape to form an ophthalmic device, and the polymerization carried out by exposure to blue-light. The device materials of the present invention are preferably cured in vitro.

Blue-light sources are commercially available and include: the Palatray CU blue-light unit (available from Heraeus Kulzer, Inc., Irvine, Calif.), the Fusion F450 blue light system (available from TEAMCO, Richardson, Tex.) and the GE 24" blue fluorescent lamp (available from General Electric Company, U.S.). A preferred blue-light source is the Palatray CU blue-light unit. Suitable blue-light sources emit light in the 400–500 nm range sufficient to activate benzoylphosphine oxide initiators. Suitable blue-light sources include sunlight and standard white fluorescent light bulbs, for example, though these sources would require longer exposure times to achieve complete cures than sources which emit light in the 400–500 nm range at higher intensities.

The intensity of the blue light from the blue-light source is preferably from about 1 to about 40 mW/cm$^2$. An intensity in the blue-light region of from about 10 to about 15 mW/cm$^2$ is more preferred. If the intensity of blue-light is too great, in addition to shrinkage problems created during curing, the device material may turn yellow or otherwise become discolored.

The length of time necessary for the device materials of the present invention to be exposed to a blue light source in order to be cured will depend upon a variety of factors, including the reactivity of the device material ingredients, the size and mass of the sample to be cured, the initiator concentration and the intensity of the blue-light source. In general, for individually cast devices, exposure times will range from about 5 minutes to about 4 hours, preferably from about 15 minutes to about 2 hours. Attempting to cure the device materials too quickly may result in compromised optical properties; too rapid cross-linking may cause shrinkage-related stresses within the cured polymer that distort the surface of the device as they are relieved.

For exposure times of about an hour or less, it is preferred that the molds containing the device materials not be opened immediately after being exposed to blue-light. Leaving the molds unopened for approximately one hour allows residual curing reactions to be completed.

The ophthalmic device materials prepared according to the present invention may be used to make almost any type of ophthalmic device, including contact lenses, intracorneal lenses and intraocular lenses. Ophthalmic lenses constructed of the disclosed materials can be of any design, but are preferably intraocular lenses (IOLs) capable of being rolled or folded and inserted through a relatively small incision. For example, the IOLs can be of what is known as a one piece or multipiece design. Typically, an IOL comprises an optic and at least one haptic. The optic is that portion which serves as the lens and the haptics are attached to the optic and are like arms that hold the optic in its proper place in the eye. The optic and haptic(s) can be of the same or different material. Haptics may be attached to the optic using conventional techniques. In a single piece lens, the optic and the haptics are formed out of one piece of material. Depending on the material, the haptics are then cut, or lathed, out of the material to produce the IOL. In addition to ophthalmic lenses, the materials prepared according to the methods of the present invention may also be used to make other ophthalmic devices including, but not limited to, keratoprostheses and corneal inlays or rings.

Molding and drilling operations are easily carried out if the device, e.g., an IOL optic, is molded between two polypropylene mold halves. The mold containing the cured device material is then placed on a lathe and the desired shape is lathe cut. The mold may then be easily mounted to carry out any drilling operations prior to removing the mold halves. Both the lathing and drilling operations may be facilitated by cooling the mold/device in a freezer to less than 10° C. and preferably less than 0° C. prior to each of these operations. If premature release of one or both mold halves occurs, it may be necessary to use clamps or alternative mold materials or to treat the surface of the mold halves.

The invention will be further illustrated by the following examples which are intended to be illustrative, but not limiting.

EXAMPLES

The following mixtures shown below in Table 1 were prepared and transferred into molds for curing:

TABLE 1*

|  | 1 | 2 | 3 |
|---|---|---|---|
| HEMA | 99 |  |  |
| NVP |  | 75 | 100 |
| STYRENE |  | 25 |  |
| BDDA | 1 | 1 |  |

HEMA = 2-hydroxyethylmethacrylate
NVP = N-vinyl pyrrolidone (passed through acidic alumina)
BDDA = 1,4-butanediol diacrylate
*All values are expressed as parts by weight.

The compositions of Examples 1–3 were then cured according to each of three cure profiles as indicated below in Table 2: a thermal cure system using the thermal initiator Perkadox 16 and a curing temperature of 70° C. for 1 hour; and two photoinitiators, camphorquinone and Lucirin® TPO, respectively, using a blue-light source with exposure times of 15, 30 and 60 minutes. After completing the cure profile, all molds were left unopened for approximately 1 hour. After opening the molds, physical appearance was recorded. "Liquid" indicates that the sample did not appear to cure to any significant extent. "Gel-slime" indicates that the sample cured to some extent, but still appeared to be primarily a liquid. "Gel" indicates that the sample cured to a loose solid. "Solid" indicates that the sample appeared to cure thoroughly or completely.

After the physical appearance of each sample was recorded, the samples rated "solid" were extracted in acetone. These samples were weighed ("initial weight"), placed into hot (near boiling) acetone for two hours, and then dried for two hours in an air-circulating oven. After drying, the samples were weighed again ("final weight"). The percent extractables were calculated as follows: (initial weight–final weight)/(initial weight)×100. For samples rated "liquid," no weight measurements were taken; % extractables for these samples was estimated to be 100%. For samples rated "Gel-slime" or "Gel" no weight measurements were taken; % extractables for these samples was estimated to be >95%. The physical appearance and the level of extractables for each of the samples of Table 1 are shown below in Table 2.

TABLE 2

| Cure Profile Initiator (concentration) | 1 hr/70 C oven Perkadox-16 (1%) | 15/30/60 min 14 mW/cm2 blue light dl-Camphorquinone (0.5%) | | | | | 15/30/60 min 14 mW/cm2 blue light Lucirin ® TPO (0.5%) |
| --- | --- | --- | --- | --- | --- | --- | --- |
| Example # | | Cure Results | | | | | |
| 1 | solid | gel-slime/gel-slime/solid | | | | | solid/solid/solid |
| 2 | liquid | liquid/liquid/liquid | | | | | liquid/liquid/liquid |
| 3 | liquid | gel/gel/gel | | | | | solid/solid/solid |
| EXAMPLE # | | % ACETONE EXTRACTABLES* | | | | | |
| 1 | <1 | >95 | >95 | 3.0 | <1 | <1 | <1 |
| 2 | 100 | 100 | 100 | 100 | 100 | 100 | 100 |
| 3 | 100 | ND | ND | ND | ND | ND | ND |

*ND = not determined

The results of Table 2 are discussed with reference to the type of device-forming monomer(s) present in the samples:

Example 1
a) Hydroxyalkyl methacrylate polymers

The TPO-initiated system cured very well even after the shortest exposure time (15 minutes), while the CQ-initiated system did not cure well until one hour of exposure—and even at this exposure, extractables were three times higher than the TPO-cured system at the shortest exposure time. 2-Hydroxyethyl methacrylate (HEMA) is typically rapidly cured—yet the CQ-initiated system still gave a sluggish cure.

Examples 2 & 3
b) Vinyl monomers

The NVP/styrene sample (Ex. 2) was not cured well with any of the initiators. The NVP sample (Ex. 3) appeared to cure poorly with CQ but well with TPO. The NVP sample apparently dissolved when extracted with acetone, however. It is presumed that this result may be explained by a non-cross-linked nature of the polyvinylpyrrolidone.

Figure 2:
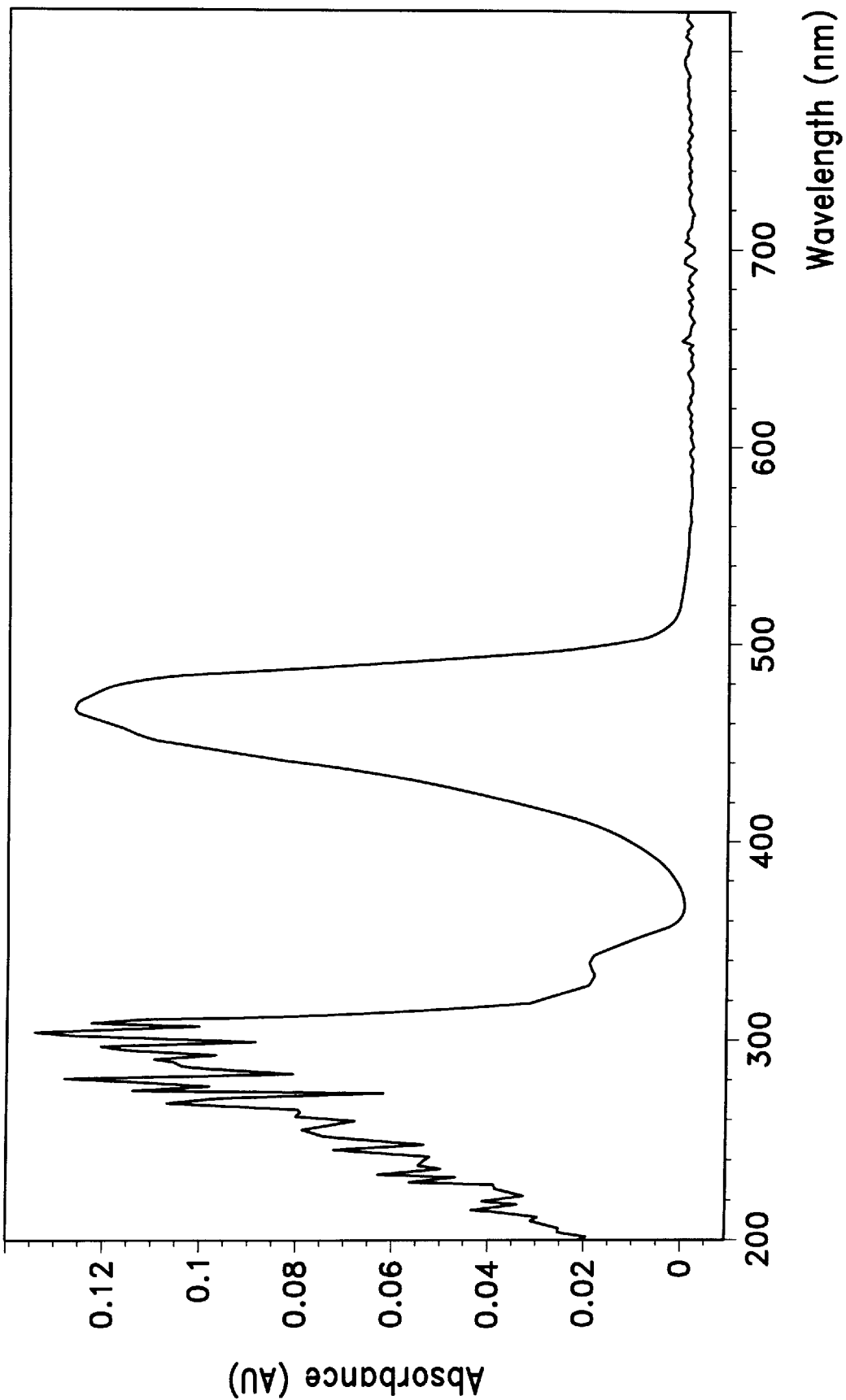
FIG. 2 shows a sample UV-visible spectrum of the alpha-diketone initiator camphorquinone in a 2-phenylethyl acrylate solvent.

The superior results obtained with TPO are surprising in view of the fact that CQ has a greater absorbency in the blue-light region than does TPO (see FIGS. 1 and 2), and thus would be expected to have the higher activity.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A method of preparing a foldable, acrylic, high refractive index ophthalmic material comprising the steps of:
   a) preparing a device-forming mixture comprising a benzoylphosphine oxide photoinitiator, an UV-absorbing chromophore and one or more hydrophilic device-forming monomers selected from the group consisting of: 2-hydroxyethylmethacrylate; 2-hydroxyethylacrylate; N-vinylpyrrolidone; glyceryl methacrylate; glyceryl acrylate; polyethylene oxide mono and dimethacrylates; and polyethylene oxide mono- and diacrylates; and
   b) exposing the mixture to a blue-light source for a period of time sufficient to cure the device forming mixture.

2. The method of claim 1 wherein the hydrophilic monomer is selected from the group consisting of: 2-hydroxyethylmethacrylate and N-vinylpyrrolidone.

3. The method of claim 1 wherein the device material has a glass transition temperature no greater than 25° C. and an elongation of at least 150%.

4. The method of claim 1 wherein the total amount of hydrophilic monomer present in the device-forming mixture is at least 50% (w/w).

5. The method of claim 4 wherein the total amount of hydrophilic monomer present in the device-forming mixture is at least 70% (w/w).

6. The method of claim 5 wherein the total amount of hydrophilic monomer present in the device-forming mixture is at least 80% (w/w).

7. The method of claim 1 wherein the device forming mixture further comprises one or more additional device-forming monomers selected from the group consisting of: acrylic acid; $C_1$–$C_8$ arylalkylacrylates; $C_1$–$C_8$ alkylacrylates; $C_1$–$C_8$ cycloalkylacrylates; N-alkylacrylamides (where alkyl=$C_1$–$C_4$); phenoxyalkylacrylates (where alkyl= $C_1$–$C_8$); and their corresponding methacrylates.

8. The method of claim 7 wherein the total amount of additional device forming monomer is 45% (w/w) or less.

9. The method of claim 1 wherein the benzoylphosphine oxide initiator is selected from the group consisting of: 2,4,6-trimethyl-benzoyldiphenylophosphine oxide; bis-(2,6-dichlorobenzoyl)-4-N-propylphenyl-phosphine oxide; and bis-(2,6-dichlorobenzoyl)-4-N-butylphenylphosphine oxide.

10. The method of claim 9 wherein the benzoylphosphine oxide initiator is 2,4,6-trimethyl-benzoyldiphenylphosphine oxide.

11. The method of claim 1 wherein the amount of benzoylphosphine oxide initiator is less than about 3% (w/w).

12. The method of claim 1 wherein the amount of benzoylphosphine oxide initiator is about 1% (w/w).

13. The method of claim 1 wherein the device forming mixture further comprises one or more ingredients selected from the group consisting of copolymerizable cross-linking monomers and blue-light absorbing chromophores.

14. The method of claim 1 wherein the blue-light source has an intensity of from about 1 to about 40 mW/cm$^2$ and the period of time in which the device forming mixture is exposed to the blue-light source is from about 5 minutes to about 4 hours.

15. The method of claim 14 wherein the bluelight source has an intensity of from about 10 to about 15 mW/cm$^2$.

* * * * *